US008523867B2

(12) United States Patent
Rauscher et al.

(10) Patent No.: US 8,523,867 B2
(45) Date of Patent: Sep. 3, 2013

(54) ORTHOPAEDIC REAMER

(75) Inventors: Markus Rauscher, Steckborn (CH); Urs Gersbach, Winterthur (CH)

(73) Assignee: Zimmer GmbH, Winterthur (CH)

( * ) Notice: Subject to any disclaimer, the term of this patent is extended or adjusted under 35 U.S.C. 154(b) by 357 days.

(21) Appl. No.: 12/846,336

(22) Filed: Jul. 29, 2010

(65) Prior Publication Data

US 2011/0028977 A1  Feb. 3, 2011

Related U.S. Application Data

(60) Provisional application No. 61/230,232, filed on Jul. 31, 2009, provisional application No. 61/233,940, filed on Aug. 14, 2009.

(51) Int. Cl.
*A61B 17/32* (2006.01)

(52) U.S. Cl.
USPC ............ 606/80; 606/79; 606/81; 606/180

(58) Field of Classification Search
USPC .......... 606/79–81, 84–85, 170–180; 175/377
See application file for complete search history.

(56) References Cited

U.S. PATENT DOCUMENTS

| | | | | |
|---|---|---|---|---|
| 5,376,092 A | * | 12/1994 | Hein et al. | 606/81 |
| 5,702,415 A | * | 12/1997 | Matthai et al. | 606/178 |
| 5,755,719 A | | 5/1998 | Frieze et al. | |
| 5,891,149 A | | 4/1999 | Young et al. | |
| 5,897,558 A | * | 4/1999 | Frieze et al. | 606/81 |
| 5,919,195 A | | 7/1999 | Wilson et al. | |
| 5,976,144 A | | 11/1999 | Fishbein et al. | |
| 6,221,076 B1 | | 4/2001 | Albrektsson et al. | |
| 6,245,074 B1 | | 6/2001 | Allard et al. | |
| 6,428,543 B1 | | 8/2002 | Salyer | |
| 6,916,322 B2 | | 7/2005 | Jesch | |
| 6,918,914 B2 | | 7/2005 | Bauer | |
| 6,951,563 B2 | | 10/2005 | Wolford | |
| 7,048,740 B2 | | 5/2006 | White et al. | |
| 7,588,572 B2 | | 9/2009 | White et al. | |
| 7,621,915 B2 | | 11/2009 | Frederick et al. | |
| 8,282,661 B2 | * | 10/2012 | Eckman | 606/160 |
| 2005/0228390 A1 | | 10/2005 | Cutshall et al. | |
| 2007/0276396 A1 | | 11/2007 | McCarthy | |
| 2008/0147070 A1 | * | 6/2008 | Michel et al. | 606/80 |
| 2008/0195106 A1 | | 8/2008 | Sidebotham et al. | |
| 2008/0215055 A1 | | 9/2008 | Stone | |

(Continued)

FOREIGN PATENT DOCUMENTS

| | | |
|---|---|---|
| DE | 2250739 A1 | 4/1974 |
| DE | 3404123 A1 | 6/1985 |

(Continued)

OTHER PUBLICATIONS

International Preliminary Report on Patentability mailed Jan. 31, 2012 from the International Bureau including the Written Opinion of International Application No. PCT/EP2010/004684.

(Continued)

*Primary Examiner* — Todd Manahan
*Assistant Examiner* — Jessica Weiss
(74) *Attorney, Agent, or Firm* — Schwegman, Lundberg & Woessner P.A.

(57) ABSTRACT

An orthopaedic reamer is provided for preparing a bone socket, such as the glenoid of the scapula, to receive a prosthetic glenoid component. The orthopaedic reamer includes an elongate shaft and an oblong cutting head, such as a cutting head having an oval or elliptical shape.

22 Claims, 4 Drawing Sheets

(56) References Cited

U.S. PATENT DOCUMENTS

| | | |
|---|---|---|
| 2008/0306482 A1 | 12/2008 | Muller |
| 2009/0116920 A1 | 5/2009 | Bae |
| 2010/0087830 A1* | 4/2010 | Dace et al. .................. 606/99 |
| 2010/0292699 A1* | 11/2010 | Favre ............................ 606/80 |

FOREIGN PATENT DOCUMENTS

| | | | |
|---|---|---|---|
| DE | 102005058107 A1 | | 7/2007 |
| GB | 2406278 A | | 3/2005 |
| GB | 2406278 | * | 8/2007 |
| WO | WO2007073606 | * | 5/2007 |
| WO | WO2007/097749 A1 | | 8/2007 |

OTHER PUBLICATIONS

The published International Application No. PCT/EP2010/004684, published Feb. 3, 2011 as WO2011/012318A1.

* cited by examiner

ORTHOPAEDIC REAMER

CROSS REFERENCE TO RELATED APPLICATION

This application claims priority from U.S. Provisional Patent Application Ser. No. 61/230,232, filed Jul. 31, 2009, and from U.S. Provisional Patent Application Ser. No. 61/233,940, filed Aug. 14, 2009, both entitled "ORTHOPAEDIC REAMER," the disclosures of which are hereby expressly incorporated by reference herein in their entirety.

BACKGROUND

1. Field of the Invention

The present invention relates to the field of orthopaedics. More particularly, the present invention relates to an apparatus and method for reaming a bone socket, such as the glenoid of the scapula, to receive a prosthetic component.

2. Description of the Related Art

A patient's shoulder or glenohumeral joint includes a generally ball-shaped head of the humerus that articulates with the glenoid or socket of the scapula. In a healthy shoulder joint, articular cartilage covers the articular portions of the humeral head and the glenoid to facilitate movement of the shoulder joint. However, due to disease or traumatic injury, for example, the articular cartilage of the shoulder joint may be damaged or degenerated.

Such changes to the shoulder anatomy may necessitate replacement of all or part of the natural shoulder joint with prosthetic shoulder components. For example, the natural humeral head may be replaced with a prosthetic humeral component. Also, the glenoid may be replaced with a prosthetic glenoid component. When glenoid replacement is indicated, the glenoid may be resurfaced and shaped to accept the prosthetic glenoid component. The prosthetic glenoid component generally includes an articular surface that is engaged by the prosthetic humeral component.

SUMMARY

The present invention provides an orthopaedic reamer for preparing a bone socket, such as the glenoid of the scapula, to receive a prosthetic glenoid component, and a method for using the same. The orthopaedic reamer includes an elongate shaft and an oblong cutting head, such as a cutting head having an oval or elliptical shape.

According to an embodiment of the present invention, an orthopaedic reamer is provided for preparing a patient's bone. The orthopaedic reamer includes a shaft that is rotatable about a longitudinal axis and a cutting head coupled to the shaft to transmit rotation of the shaft about the longitudinal axis to the cutting head. The cutting head of the orthopaedic reamer includes an oblong body having a peripheral wall that defines an outer perimeter of the cutting head, a length of the oblong body exceeding a width of the oblong body, a first blade that extends radially outwardly from the longitudinal axis toward the peripheral wall of the oblong body, and a second blade that extends radially outwardly from the longitudinal axis toward the peripheral wall of the oblong body in a direction transverse to the first blade.

According to another embodiment of the present invention, an orthopaedic reamer configured for rotation about a longitudinal axis is provided to prepare a patient's bone. The orthopaedic reamer includes a shaft and a cutting head coupled to the shaft. The cutting head of the orthopaedic reamer includes an oblong body having a peripheral wall that defines an outer perimeter of the cutting head, a first dimension of the oblong body exceeding a second dimension of the oblong body, and a plurality of blades spaced radially about the longitudinal axis, the plurality of blades extending radially outwardly toward the peripheral wall of the oblong body.

According to yet another embodiment of the present invention, a method is provided for preparing a glenoid of a patient's scapula using an orthopaedic reamer having an oblong cutting head that defines a bone-contacting surface. The method includes the steps of: accessing the patient's scapula; inserting the oblong cutting head through an incision, a length of the oblong cutting head inserted through the incision exceeding a width of the oblong cutting head inserted through the incision; and positioning the bone-contacting surface of the oblong cutting head against the glenoid of the patient's scapula.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 1:
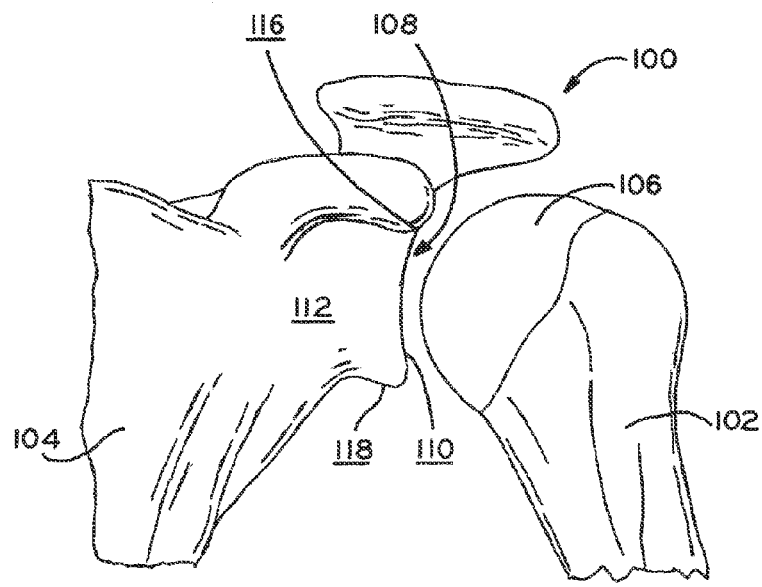
FIG. 1 is an anterior perspective view of a patient's natural shoulder joint, including a humerus and a scapula.
Figure 2:
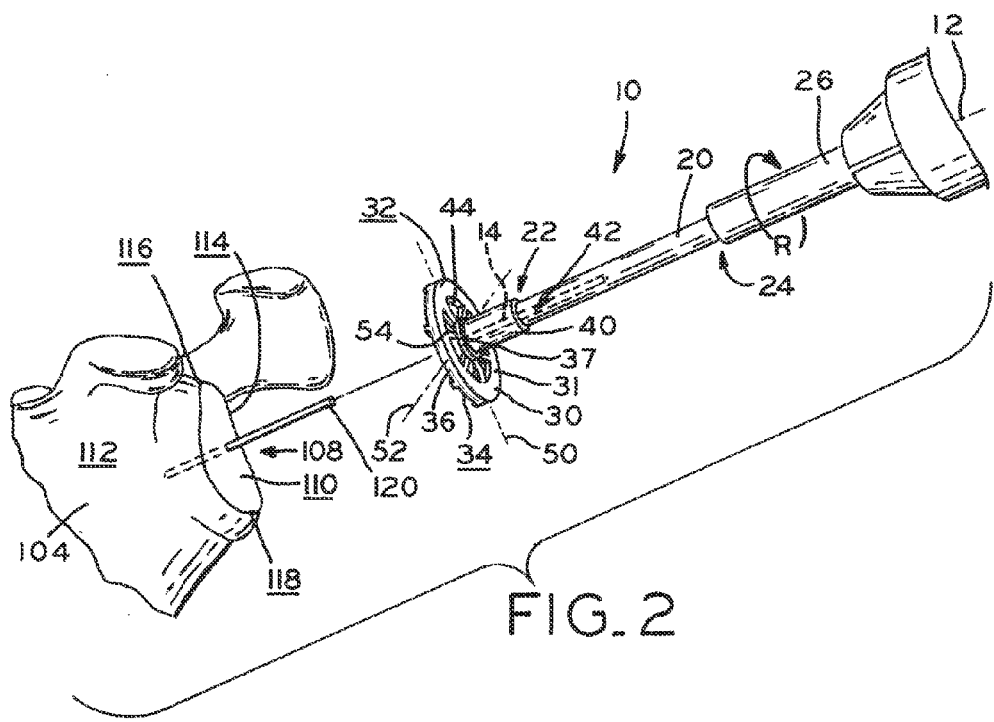
FIG. 2 is a perspective view of an exemplary reamer of the present invention being moved toward the scapula of FIG. 1, the reamer including a shaft and a cutting head.

A patient's left shoulder joint 100 is illustrated in FIG. 1. The natural shoulder joint 100 includes humerus 102 and scapula 104. Humerus 102 of shoulder joint 100 includes a generally ball-shaped head 106. Scapula 104 of shoulder joint 100 includes glenoid or socket 108 having glenoid surface 110. During movement of the natural shoulder joint 100, head 106 of humerus 102 articulates within glenoid 108 of scapula 104 against glenoid surface 110. As shown in FIG. 2, glenoid 108 of scapula 104 is bordered by anterior surface 112, posterior surface 114, superior surface 116, and inferior surface 118 of scapula 104.

Figure 5:
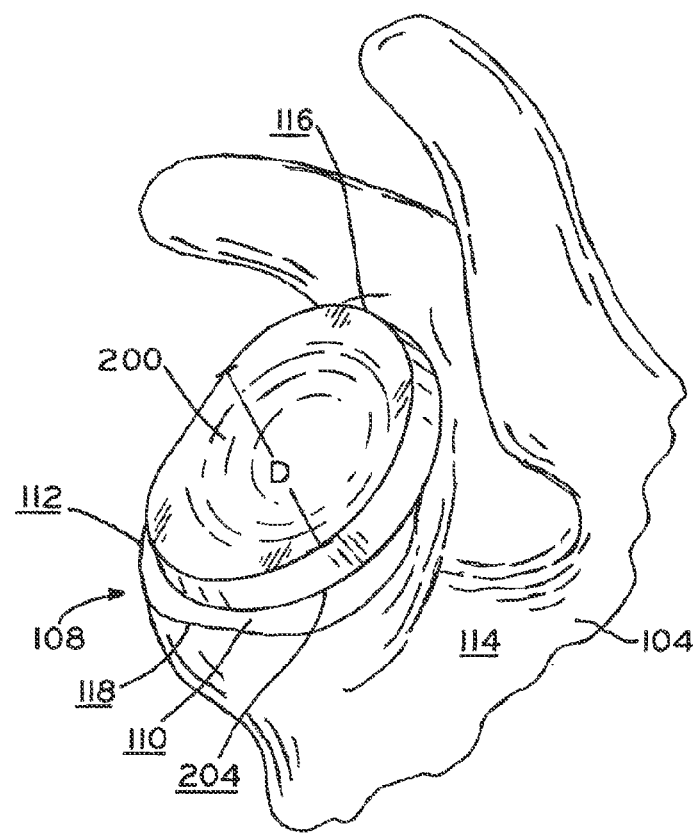
FIG. 5 is a posterior perspective view of a prosthetic glenoid component implanted into the scapula of FIG. 1.

If scapula 104 of the natural shoulder joint 100 suffers traumatic injury or degenerative changes, for example, a surgeon may replace the natural glenoid 108 with prosthetic glenoid component 200, as shown in FIG. 5. An exemplary procedure for preparing scapula 104 to receive prosthetic glenoid component 200 is set forth below. Additional information regarding the preparation of scapula 104 is set forth in U.S. Pat. No. 7,294,133, entitled "Method and Apparatus for Preparing a Glenoid Surface," filed Jun. 2, 2005, the disclosure of which is hereby expressly incorporated by reference herein.

Figure 6:
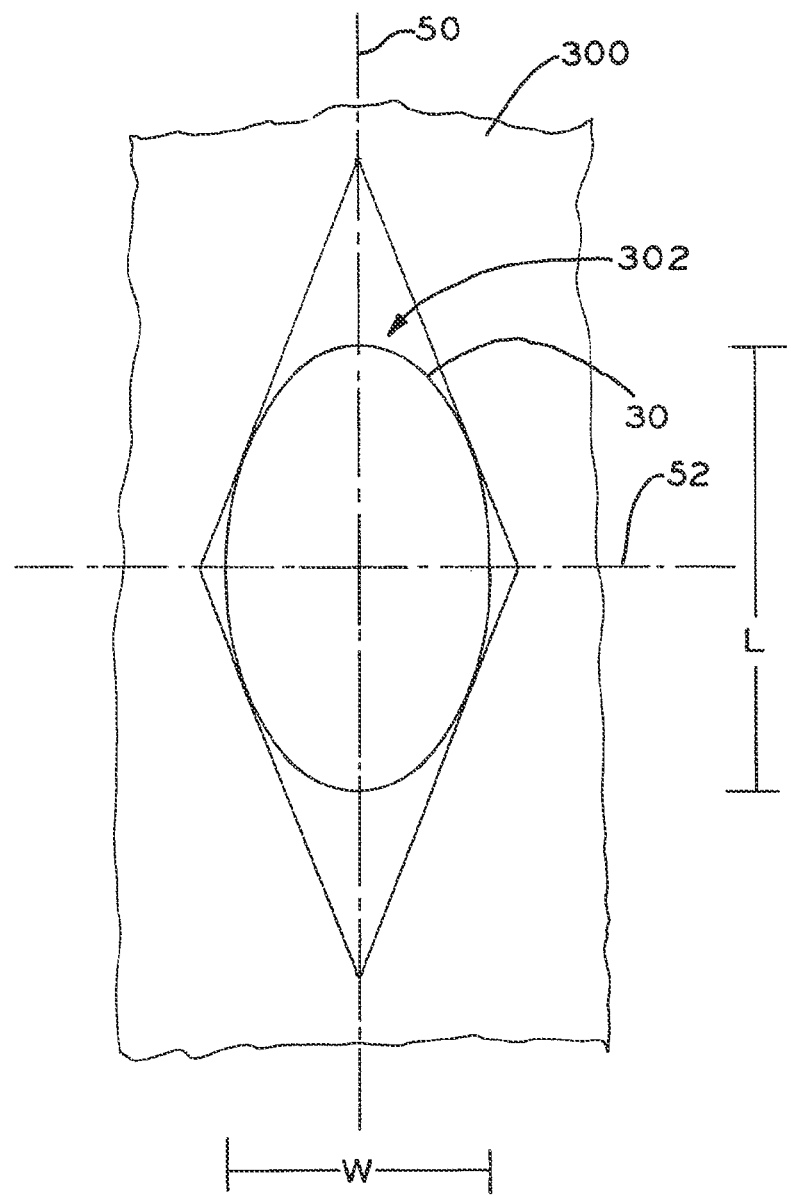
FIG. 6 is a schematic view of the cutting head of FIG. 3 being inserted through an incision in a patient's soft tissue.

First, the surgeon exposes glenoid surface 110 of the natural shoulder joint 100, as shown in FIG. 2. This step involves making an incision 302 into the patient's skin or other soft tissue 300, as shown in FIG. 6, and moving shoulder muscles away from glenoid surface 110.

Next, the surgeon inserts guide pin 120 medially into glenoid surface 110 of glenoid 108, as shown in FIG. 2. Guide pin 120 may be a 3 millimeter K-wire, for example. According to an exemplary embodiment of the present invention, this step may be performed using an alignment guide component (not shown) that references scapula 104 to properly position and orient guide pin 120 in glenoid 108. An exemplary alignment guide component is shown and described in U.S. patent application Ser. No. 12/846,277, entitled "Glenoid Alignment Tool," filed Jul. 29, 2010, the disclosure of which is hereby expressly incorporated by reference herein. Once inserted into the patient's bone, guide pin 120 projects laterally beyond glenoid surface 110, as shown in FIG. 2, to serve as an alignment feature for instruments used to prepare glenoid surface 110. In particular, guide pin 120 serves as an alignment feature for reamer 10.

Figure 3:
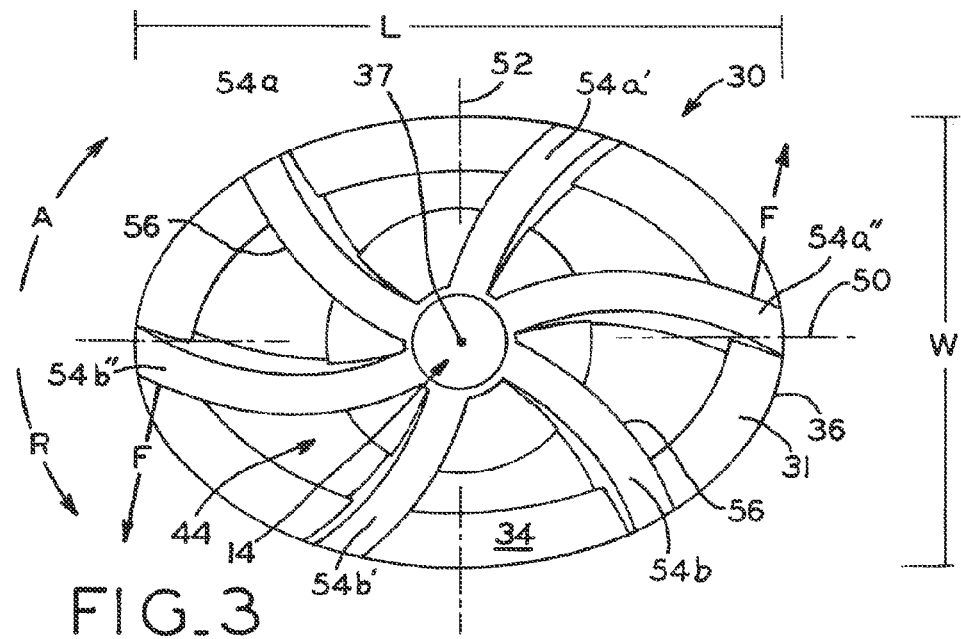
FIG. 3 is a bottom plan view of the cutting head of FIG. 2.

An exemplary reamer 10 is illustrated in FIGS. 2 and 3. Reamer 10 has longitudinal axis 12 and includes an elongate shaft 20 and cutting head 30. As shown in FIG. 2, shaft 20 and cutting head 30 of reamer 10 cooperate to define referencing bore 14 that extends along longitudinal axis 12 of reamer 10 and that is sized to receive guide pin 120 therein.

Referring to FIG. 2, shaft 20 of reamer 10 extends along longitudinal axis 12 from first end 22 to second end 24. First end 22 of shaft 20 is coupled to cutting head 30 of reamer 10 to transmit rotational motion of shaft 20 to cutting head 30. For example, first end 22 of shaft 20 may be externally threaded to engage an internally threaded cutting head 30. As another example, first end 22 of shaft 20 may be non-circular in cross-section for receipt within a non-circular recess of cutting head 30. Second end 24 of shaft 20 may be attached to a suitable electrical tool 26 that is able to drive rotation of both shaft 20 and cutting head 30 about longitudinal axis 12 along arrow R.

Figure 4:
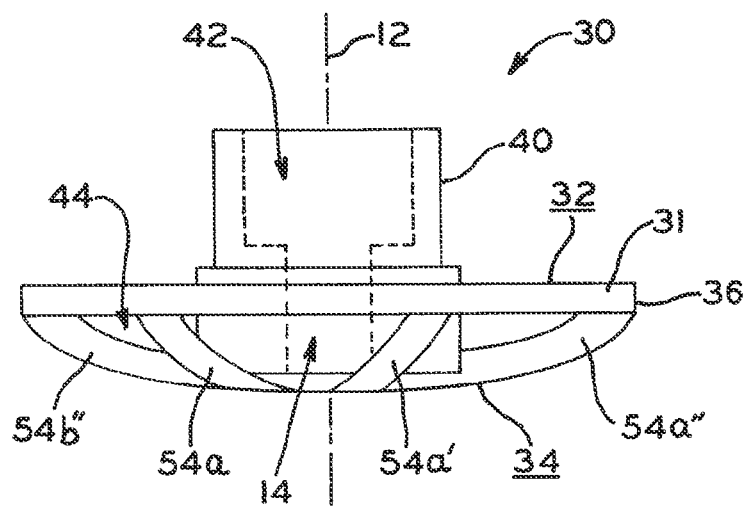
FIG. 4 is an elevational view of the cutting head of FIG. 3.

Referring to FIGS. 2-4, cutting head 30 of reamer 10 includes body 31 having first surface 32 and second bone-contacting surface 34. As shown in FIG. 4, second bone-contacting surface 34 of cutting head 30 may be slightly convex to match the slightly concave curvature of glenoid surface 110. It is also within the scope of the present invention that second bone-contacting surface 34 of cutting head 30 may be nearly flat. Body 31 of cutting head 30 also includes a continuous, smooth peripheral wall 36 that joins first surface 32 and second bone-contacting surface 34. Longitudinal axis 12 of reamer 10 extends through center 37 of cutting head 30.

Cutting head 30 of reamer 10 may further include a cylindrical wall 40 that extends upwardly from first surface 32 along longitudinal axis 12 to define chamber 42 that is sized to receive shaft 20 therein. More particularly, chamber 42 of cutting head 30 may be sized to receive first end 22 of shaft 20 therein. As mentioned above, wall 40 of cutting head 30 may be internally threaded to engage an externally threaded shaft 20, or wall 40 may define a non-circular chamber 42 that is sized to receive a non-circular shaft 20, for example. It is also within the scope of the present invention that shaft 20 may be retained within chamber 42 using a set screw or another suitable fastener.

According to an exemplary embodiment of the present invention, cutting head 30 includes at least one viewing aperture 44 that extends entirely through body 31 of cutting head 30 so that the surgeon can view glenoid surface 110 when reamer 10 is positioned proximate glenoid 108. More particularly, the at least one viewing aperture 44 extends from first surface 32 to second bone-contacting surface 34 of cutting head 30. In the illustrated embodiment of FIG. 3, a plurality of viewing apertures 44 are located radially inwardly of peripheral wall 36, the individual viewing apertures 44 being separated by radially spaced blades 54.

Referring to FIGS. 2 and 3, cutting head 30 includes first axis 50 that extends across the length L of cutting head 30 and through center 37 of cutting head 30. Cutting head 30 also includes second axis 52 that extends perpendicularly to first axis 50 across the width W of cutting head 30 and through center 37 of cutting head 30. First axis 50 may be considered a major axis of cutting head 30 and second axis 52 may be considered a minor axis of cutting head 30. As shown in FIG. 2, first axis 50 and second axis 52 of cutting head 30 are located in a plane that is perpendicular to longitudinal axis 12 of reamer 10.

Referring still to FIGS. 2 and 3, the length L of cutting head 30 along first axis 50 is greater than the width W of cutting head 30 along second axis 52, such that cutting head 30 is oblong in shape. Stated differently, body 31 of cutting head 30 projects further outwardly from shaft 20 along first axis 50 than along second axis 52. Compared to known reamers that define a circular or square shape, the shortened width W of cutting head 30 along second axis 52 allows reamer 10 to be inserted through a narrow, less invasive incision 302 in soft tissue 300, as shown in FIG. 6. This surgical benefit during insertion is achieved without impacting the span of cutting head 30 during subsequent reaming. When cutting head 30 is rotated about longitudinal axis 12 along arrow R, cutting head 30 is still able to ream a circular pattern into glenoid surface 110, as if the width W of cutting head 30 were equal to the length L of cutting head 30, even though the width W of cutting head 30 is actually less than the length L of cutting head 30.

According to an exemplary embodiment of the present invention, body 31 of cutting head 30 achieves this oblong shape with a smooth, arcuate peripheral wall 36. For example, body 31 of cutting head 30 may be provided in an oval shape about longitudinal axis 12 of reamer 10, such that peripheral wall 36 of body 31 defines a smooth outer surface of cutting head 30. As another example, body 31 of cutting head 30 may be provided in an elliptical shape about longitudinal axis 12 of reamer 10, such that peripheral wall 36 of body 31 defines a smooth outer surface of cutting head 30. It is also within the scope of the present invention that body 31 of cutting head 30 may be provided in a rectangular shape or a diamond shape, for example, preferably with smooth, rounded corners. In use, the smooth peripheral wall 36 of cutting head 30 may reduce the risk of damage to any healthy soft tissue that remains around glenoid 108.

As shown in FIGS. 3 and 4, cutting head 30 includes a plurality of radially spaced blades 54 that project downwardly from body 31 to define second bone-contacting surface 34. As discussed above, adjacent blades 54 may define viewing apertures 44 therebetween. Blades 54 extend radially outwardly from longitudinal axis 12 toward peripheral wall 36 of body 31 of cutting head 30.

According to an exemplary embodiment of the present invention, and as shown in FIG. 3, each blade 54 defines an arcuate path as it travels outwardly from longitudinal axis 12 to peripheral wall 36 of body 31 of cutting head 30. Rather than extending linearly from longitudinal axis 12 to peripheral wall 36, each blade 54 curves rearwardly along arrow A (which extends clockwise in the bottom view of FIG. 3) when approaching peripheral wall 36 of body 31. In this embodiment, first axis 50 and/or second axis 52 may be axes of symmetry that divide body 31 of cutting head 30 into symmetrical halves, but not blades 54 of cutting head 30.

Each blade 54 includes a sharp cutting face 56 that contacts and cuts bone as cutting head 30 is rotated in the direction of arrow R (which extends clockwise in the top view of FIG. 2 and counter-clockwise in the bottom view of FIG. 3). According to an exemplary embodiment of the present invention, cutting face 56 of each blade 54 curves rearwardly in the direction of arrow A as it approaches peripheral wall 36, which is opposite to the direction of rotation of arrow R. As shown in FIG. 3, cutting face 56 of each blade 54 curves to face outward (i.e., away from longitudinal axis 12 and center 37) as it approaches peripheral wall 36. As a result, force F that is normal to cutting face 56 extends outwardly from cutting head 30 (i.e., away from longitudinal axis 12 and center 37). It is within the scope of the present invention that each cutting face 56 may extend in a plane that is substantially parallel to longitudinal axis 12, or that each cutting face 56 may be ramped or angled relative to longitudinal axis 12.

As shown in FIG. 3, cutting head 30 includes three blades 54a, 54a', 54a", that originate substantially above first axis 50 and three corresponding, opposing blades 54b, 54b', 54b", that originate substantially below first axis 50. Although cutting head 30 is shown and described having six blades 54, it is within the scope of the present invention that cutting head 30 may be provided with fewer than six blades 54 or more than six blades 54. Blades 54a", 54b", span across the longer length L of cutting head 30. Blades 54a, 54a', 54b, 54b', extend transversely to blades 54a", 54b", and span across the shorter width W of cutting head 30. For this reason, blades 54a", 54b", may be longer than blades 54a, 54a', 54b, 54b'.

Each blade 54a, 54a', 54a", is oriented approximately 180 degrees from its corresponding blade 54b, 54b', 54b", about center 37 of cutting head 30 and is substantially the same shape and size as its corresponding blade 54b, 54b', 54b". As shown in FIG. 3, each blade 54a, 54a', 54a", cooperates with its corresponding blade 54b, 54b', 54b", to define an S-shaped cutting face 56. For example, blade 54a cooperates with its corresponding blade 54b to define an S-shaped cutting face 56. The balanced arrangement of blades 54a, 54a', 54a", 54b, 54b', 54b", about center 37 of cutting head 30 encourages self-centering of cutting head 30 and limits vibrations when cutting head 30 is rotated in the direction of arrow R.

In operation, and as shown in FIG. 2, the surgeon inserts guide pin 120 into referencing bore 14 of reamer 10 and positions cutting head 30 of reamer 10 over guide pin 120 and against glenoid surface 110. Then, the surgeon rotates reamer 10 about guide pin 120 to remove any remaining cartilage from glenoid surface 110 and to substantially smooth and/or level the bone stock of glenoid 108. As mentioned above, the surgeon is able to view glenoid surface 110 through viewing apertures 44 in cutting head 30. When glenoid surface 110 is properly formed, the surgeon removes reamer 10 from glenoid surface 110. After all drilling and shaping steps are completed, the surgeon also removes guide pin 120 from glenoid surface 110.

Finally, the surgeon implants prosthetic glenoid component 200 into the prepared glenoid 108. As shown in FIG. 5, prosthetic glenoid component 200 includes a concave articulating surface 202 that substantially replicates that of a healthy glenoid to restore normal joint function. It is also within the scope of the present invention that prosthetic glenoid component 200 may be part of a reverse shoulder implant system, such that the final prosthetic glenoid component 200 is a convex component designed to articulate with a concave prosthetic humeral component (not shown). Also, prosthetic glenoid component 200 includes a bone-contacting undersurface 204 that achieves intimate contact with the prepared glenoid surface 110.

To achieve an exemplary anatomical fit of prosthetic glenoid component 200 in the prepared glenoid 108, cutting head 30 of reamer 10 is provided to mimic the size and shape of prosthetic glenoid component 200. For example, the curvature of second bone-contacting surface 34 of body 31 of cutting head 30 is substantially the same as the curvature of undersurface 204 of prosthetic glenoid component 200. Also, the length L of body 31 of cutting head 30 along first axis 50 is substantially the same as the diameter D of prosthetic glenoid component 200.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic reamer for preparing a patient's bone, the orthopaedic reamer comprising:
   a shaft that is rotatable about a longitudinal axis; and
   a cutting head coupled to the shaft to transmit rotation of the shaft about the longitudinal axis to the cutting head, the cutting head comprising:
      an oblong body having a peripheral wall that defines an outer perimeter of the cutting head, a length of the oblong body exceeding a width of the oblong body, wherein the length and the width are measured perpendicular to each other and along a plane perpendicular to the longitudinal axis;
      a first blade that extends radially outwardly from the longitudinal axis toward the peripheral wall of the oblong body; and
      a second blade that extends radially outwardly from the longitudinal axis toward the peripheral wall of the oblong body in a direction transverse to the first blade.

2. The orthopaedic reamer of claim 1, wherein the oblong body is one of oval and elliptical in shape.

3. The orthopaedic reamer of claim 1, wherein the oblong body includes rounded corners.

4. The orthopaedic reamer of claim 1, wherein the first and second blades cooperate to define a convex surface of the cutting head that is configured to abut a concave surface of the patient's bone.

5. The orthopaedic reamer of claim 1, wherein the first blade spans at least a portion of the length of the oblong body and the second blade spans at least a portion of the width of the oblong body, wherein the first blade is longer than the second blade.

6. The orthopaedic reamer of claim 1, wherein the first and second blades are located radially inwardly of the peripheral wall of the oblong body.

7. The orthopaedic reamer of claim 1, wherein the first blade includes a first cutting face and the second blade includes a second cutting face that extends transversely to the first cutting face, the first and second cutting faces configured to cut into the patient's bone as the cutting head is rotated about the longitudinal axis.

8. The orthopaedic reamer of claim 7, wherein the first and second cutting faces are arcuate in shape.

9. The orthopaedic reamer of claim 7, wherein the first and second blades curve outwardly when approaching the peripheral wall of the oblong body such that a force that is normal to one of the first and second cutting faces extends outwardly from the cutting head.

10. The orthopaedic reamer of claim 1, further including a third blade that corresponds to the first blade, the third blade originating 180 degrees about the longitudinal axis from the first blade and having the same shape and size as the first blade.

11. The orthopaedic reamer of claim 10, wherein the first blade includes a first cutting face and the third blade includes a third cutting face, the first and third cutting faces configured to cut into the patient's bone as the cutting head is rotated about the longitudinal axis, the first and third cutting faces facing in opposite directions.

12. The orthopaedic reamer of claim 11, wherein the first and third cutting faces cooperate to define an S-shaped cutting face.

13. An orthopaedic reamer configured for rotation about a longitudinal axis to prepare a patient's bone, the orthopaedic reamer comprising:
    a shaft; and
    a cutting head coupled to the shaft and comprising:
        an oblong body having a peripheral wall that defines an outer perimeter of the cutting head, a first dimension of the oblong body exceeding a second dimension of the oblong body, wherein the first dimension and the second dimension are measured perpendicular to each other and along a plane perpendicular to the longitudinal axis; and
        a plurality of blades spaced radially about the longitudinal axis, the plurality of blades extending radially outwardly from the longitudinal axis toward the peripheral wall of the oblong body.

14. The orthopaedic reamer of claim 13, wherein the plurality of blades includes a first blade and a second blade adjacent to the first blade, the first and second blades being spaced apart to define a viewing aperture through the cutting head, wherein the viewing aperture increases in size toward the peripheral wall of the oblong body.

15. The orthopaedic reamer of claim 13, wherein the plurality of blades includes a first blade and a second blade that originates 180 degrees about the longitudinal axis from the first blade, the first and second blades cooperating to define an S-shaped protrusion from the oblong body.

16. The orthopaedic reamer of claim 13, wherein each of the plurality of blades defines an arcuate cutting face, the arcuate cutting faces of the plurality of blades configured to cut into the patient's bone as the cutting head is rotated about the longitudinal axis.

17. The orthopaedic reamer of claim 13, wherein the oblong body includes rounded corners.

18. A method for preparing a glenoid of a patient's scapula using an orthopaedic reamer having an oblong cutting head that defines a bone-contacting surface, the method comprising the steps of:
    accessing the patient's scapula;
    inserting the oblong cutting head through an incision, a length of the oblong cutting head inserted through the incision exceeding a width of the oblong cutting head inserted through the incision, wherein the length and the width are measured perpendicular to each other and along a plane perpendicular to the longitudinal axis, and wherein the oblong cutting head includes a plurality of blades spaced radially about the longitudinal axis, the plurality of blades extending radially outwardly from the longitudinal axis toward a peripheral wall of the oblong body; and
    positioning the bone-contacting surface of the oblong cutting head against the glenoid of the patient's scapula.

19. The method of claim 18, wherein the positioning step comprises positioning a convex bone-contacting surface of the oblong cutting head against a concave surface of the glenoid.

20. The method of claim 17, wherein each blade has a cutting face, the method further comprising the step of rotating the orthopaedic reamer about a longitudinal axis in a first direction with the cutting faces of the plurality of blades cutting into the patient's scapula.

21. The method of claim 20, wherein the cutting faces of the plurality of blades curve in a second direction opposite the first direction as the plurality of blades extend radially outwardly from the longitudinal axis.

22. The method of claim 18, further comprising the step of implanting a prosthetic glenoid component into the patient's scapula, the prosthetic glenoid component having a diameter that exceeds the width of the oblong cutting head.

* * * * *

UNITED STATES PATENT AND TRADEMARK OFFICE
CERTIFICATE OF CORRECTION

| | | |
|---|---|---|
| PATENT NO. | : 8,523,867 B2 | Page 1 of 1 |
| APPLICATION NO. | : 12/846336 | |
| DATED | : September 3, 2013 | |
| INVENTOR(S) | : Rauscher et al. | |

It is certified that error appears in the above-identified patent and that said Letters Patent is hereby corrected as shown below:

In the Claims

Column 8, line 30, in Claim 20, delete "claim 17," and insert --claim 18,--, therefor Signed and Sealed this
Eighteenth Day of February, 2014

Michelle K. Lee
*Deputy Director of the United States Patent and Trademark Office*